United States Patent
Mauze et al.

(10) Patent No.: US 6,379,969 B1
(45) Date of Patent: Apr. 30, 2002

(54) OPTICAL SENSOR FOR SENSING MULTIPLE ANALYTES

(75) Inventors: Ganapati R. Mauze, Sunnyvale; Bo Curry, Redwood City, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/517,259

(22) Filed: Mar. 2, 2000

(51) Int. Cl.[7] .............................................. G01N 21/64
(52) U.S. Cl. .............................. 436/68; 436/74; 436/79; 436/95; 436/98; 436/163; 436/172; 422/82.05; 422/82.07; 422/82.08
(58) Field of Search .............................. 436/74, 68, 79, 436/95, 98, 163, 172; 422/82.05, 82.07, 82.08

(56) References Cited

U.S. PATENT DOCUMENTS

| | | | |
|---|---|---|---|
| 5,057,277 A | 10/1991 | Mauze et al. | 422/56 |
| 5,462,989 A | 10/1995 | Mauze et al. | 524/707 |
| 5,698,089 A | 12/1997 | Lewis et al. | 205/787 |
| 5,788,833 A | 8/1998 | Lewis et al. | 205/787 |

OTHER PUBLICATIONS

Raymond F. Chen and Carrie H. Scott, Special Review, "Atlas of Fluorescence Spectra and Lifetimes of Dyes Attached to Protein", Analytical Letters, 18(a4), 393–421 (1985).

Jason M. Price, Wenying Xu, J. N. Demas and B. A. DeGraft, "Polymer–Supported pH Sensors Based on Hydrophobically Bound Luminescent Ruthenium(II) Complexes"; Anal. Chem. 1998, 70, 265–270.

Ute Kosch, Ingo Klimant, Tobias Werner, and Otto S. Wolfbels, "Strategies to Design pH Optodes with Luminiescence Decay Times in the Microsecond Time Regime", Anal. Chem. 1998, 70, 3892–3897.

Wenying Xu, Robert Clayton McDonough, III, Brandi Langsdorf, J. N. Demas, and B. A. DeGraft; "Oxygen Sensors Based on Luminescence Quenching: Interactions of Metal Complexes with the Polymer Supports", Analytical Chemistry, 1994, 66, 4133–4141.

Ganapati R. Mauze and Robert R. Holloway, "A non-crosslinked organosilicon matrix for luminescence quenching based fiber optic oxygen sensors", Fiber Optic Sensors in Medical Diagnostics (1993) 78/SPIE vol. 1986.

(List continued on next page.)

Primary Examiner—Jeffrey Snay

(57) ABSTRACT

A device for analyzing simultaneously multiple analytes in a fluid of unknown composition. The device includes a plurality of sensors, a light source for providing light to shine on the sensors, light detectors, and a processor. The sensors are exposed to a sample of the fluid of unknown composition. The plurality of sensors includes groups of sensors, each group targeting a specific analyte and including one or more sensors that contain an analyte-specific chemical that interacts more specifically with one analyte than with some other analytes to be analyzed. Each sensor in each group has a different chemical interacting with the analyte to target it. The light source shines light on the sensors of the plurality of sensors to cause light interaction with the sensors. The differences in the sensors lead to differences in the light interaction. The light detectors detects the light interaction by the sensors. The processor analyzes the light interaction by the sensors to take into account interference in light interaction among the analytes, thereby determining the concentration of each of the analytes in the fluid.

24 Claims, 3 Drawing Sheets

OTHER PUBLICATIONS

David S. Ballantine, Jr., Susan L. Rose, Jay W. Grate and Hank Wohltjen, "Correlation of Surface Acoustic Wave Device Coating Responses with Solubility Properties and Chemical Structure Using Pattern Recognition"; Analytical Chemistry, 1986, 58, 3058–3066.

Otto S. Wolfbeis, Ingo Klimant, Tobias Werner, Christian Huber, Ute Kosch, Christian Krause, Gerhard Neurauter, Axel Durkop; Set of luminescence decay time based chemical sensors for clinical applications; Sensors and Actuators B 51 (1998) 17–24.

Gilbert Strang, "Linear Algebra and its Applications", 2nd Edition, Massachussetts Institute of Technology, Chapter 9, pp. 192–235.

OPTICAL SENSOR FOR SENSING MULTIPLE ANALYTES

FIELD OF THE INVENTION

The present invention relates to devices and methods for sensing multiple analytes in fluids, and more specifically to devices and methods for determining the concentration of multiple analytes simultaneously in an unknown fluid sample using optical interrogation.

BACKGROUND

Analytical chemistry has been instrumental in providing healthier and more comfortable living for billions around the world. For example, to protect the environment, samples of water, air, microorganisms, tissues from plants and animals are analyzed. In the medical field, samples of body tissues and physiological fluids are analyzed on a routine basis to provide information on patients, for diagnosis as well as for monitoring purposes. In the past, analyses were mostly done by collecting samples and bringing them to a laboratory for analysis by large, expensive pieces of equipment. In other cases, analyses were even done manually using wet chemistry. To determine the concentration or presence of different analytes in an unknown sample, often the unknown sample, such as a liquid, has to be divided into many portions and analyzed one analyte at a time. Thus, the analysis of multiple analytes in an unknown sample is cumbersome and time-consuming.

Some examples of instruments that can sense multiple analytes simultaneously are AVL Opti CCA, Chiron Centaur, Instrumentation Laboratory GEM 201, I-STAT Portable Analyzer, etc. AVL Opti CCA is a portable analyzer that provides the measurement of pH, total hemoglobin, oxygen saturation, blood gas, and electrolyte parameters. The analyzer uses Opti CCA cassette system, which is a single use cassette system incorporating optical sensing technology. The cassette contains optical fluorescence sensors, one for each of pH, $PCO_2$, $PO_2$, $Na^+$, $K^+$, $iCa^{++}$ (ionic calcium) and $Cl^-$. The analytes $SO_2$ and tHb (total hemoglobin) are measured using optical absorbance and reflectance, respectively. Diameterics IRMA is also a portable analyzer that measures pH, $PCO_2$, $PO_2$, $Na^+$, $K^+$, $iCa^{++}$, $Cl^-$, Hct (hematocrit), and glucose. For Diameterics IRMA, disposable cartridges are configured to provide several combinations of these parameters using one electrochemical sensor for each parameter. The glucose cartridge is a stand alone cartridge that uses optical reflectance technology. The I-STAT device also uses cartridges based on electrochemical sensors, one for each parameter. Several different cartridges are available for different combinations of the parameters that include pH, $PCO_2$, $PO_2$, $Na^+$, $K^+$, $iCa^{++}$, $Cl^-$, Hct, glucose, blood urea nitrogen (BUN), and Creatinine. It is to be noted that although a large number of parameters can be measured using these analyzers, none of the analyzers can be used to analyze all the parameters on one cartridge. Moreover, the analyzers often use a combination of both optical and electrochemical sensing technologies.

Although simultaneous analysis of a plurality of analytes have been done, the analytical instruments are often complex. For example, prior methods in sensing multiple analytes optically involve using multiple optical sensors, each of which is optimized for sensing one specific analyte. The sensors are designed to be specific to the analyte they target and not responsive to any other analyte that might be present in the sample. One disadvantage of such methods is that one has to design a highly specific sensor. Designing for such high specificity is costly, time-consuming, and not always practical. Moreover, the sensors so designed can be used only in well-defined samples, which are known not to contain interfering species of analytes. Failure to ensure such specificity in the sensor could lead to unreliable measurements. For example, some blood glucose sensors cannot be used when acetaminophen is present in the blood sample. Another disadvantage of this design is that each of the sensors requires a different method on interrogation. For example, a pH sensor may be based on optical absorbance of an indicator at one wavelength while an oxygen sensor may be based on fluorescence quenching at another wavelength. A third method, such as colorimetry, may have to be used for glucose sensing, and so on, for other analytes. As a result, the instrument for analyzing multiple components may be complicated, expensive, bulky, and highly power-consuming.

Recently, Wolfbeis et al., "Set of luminescent decay time based chemical sensors for clinical applications", *Sensors and Actuators* B 51 (1998) 17–24, described a method of making optical sensors for several species that can be interrogated with one optical source and one detector. Although it would appear that an instrument based on this concept should be simple and inexpensive, the sensors themselves are highly non-selective. Wolfbeis et al. have shown that these sensors respond to pH. Therefore, such sensors would be unsuitable in an environment in which the pH changes. Moreover, prior literature, such as Mauze et al, "Non-crosslinked Organosilicon matrix for Luminescent Quenching based Fiber Optic Oxygen Sensors" *SPIE Proceedings*, Vol. 1886, (1993), has shown that the luminophore of these sensors is also oxygen sensitive. These sensors, as described by Wolfbeis et al., are therefore not as such applicable for measurements in changing oxygen environment either.

Another type of prior sensing devices utilize arrays of sensors that are highly non-specific to the volatile analytes in the sample. Such devices are described in, for example, U.S. Pat. Nos. 5,698,089, 5,788,833, and in Ballantine et al., *Anal Chem.* 1986, 58, 3058–3066. Such arrays consist of sensors that measure physical, optical, or electrical properties, such as density, refractive index or electrical resistance, respectively, which change in relation to the concentrations of the species that penetrate to the sensing element of the sensors. The changes in such properties are measured and the data are analyzed using pattern recognition techniques to determine the concentration of each species. Such sensors have a limited dynamic range dictated by the properties of the sensing region. Moreover, these sensing arrays can be used only for analyzing volatile species. These sensors respond to any species that penetrates the sensing region. Calibration models or training sets have to be designed to include all such species that might be present in the sample. Thus they are prone to failure when an outliner species is encountered.

Designing a sensor that responds only to one analyte is a very difficult task. Many sensors that have been tried were abandoned because interferences by one or more other analytes could not be removed. Often it is just one species that interferes with the measurement. In such cases, attempts have been made to design a sensor specifically for the interfering species without interference from others and mathematically correct for the interference. But such an added sensor requires a new method of interrogating the sensor. This adds complexity to the instrument. The challenge is particularly daunting when a large number of analytes are to be measured and many species interfere with one another. Often it is not possible to make a highly specific sensor for an interfering species.

SUMMARY

There is a need for a reliable method of analyzing multiple species in a sample using a simple instrument, for example, a single source-detector unit. Moreover, it is desirable to ensure that the devices do not respond in an intractable way to the other non-target known or unknown species that might be present in the sample. It is also desirable to make the device applicable to non-volatile species as well as to the volatile species in the sample. The present invention meets these needs and provides a technique for analyzing multiple analytes simultaneously (for example, the analytes in a sample of a liquid of unknown composition). The present technique uses a plurality of sensors to sense a plurality of analytes wherein some of the analytes may interfere with the sensors that sense other analytes and relates the responses of the sensors such that the analytes are sensed accurately in spite of the fact that the analytes may be interfering with one another.

In one aspect, the present invention provides an apparatus for analyzing multiple analytes in an unknown fluid (i.e., sample of an unknown liquid composition) simultaneously. The apparatus includes a plurality of sensors each for exposing to a sample of the unknown. The plurality of sensors includes groups of sensors wherein each group targets a specific analyte and includes one or more sensors including an analyte-specific chemical that interacts more specifically with one analyte than with other analytes to be analyzed. Each sensor in a group has a different chemical interacting specifically with the analyte. A light source is present in the apparatus for providing light to shine on the sensors to cause light interaction with the sensors. Differences in the sensors lead to differences in light interaction with the sensors. Detectors are used to determine the light interaction by the sensors. A processor is used for analyzing the light interaction by the sensors to take into account interference in light interaction among the analytes, thereby determining the concentration of each of the analytes in the unknown fluid. The present invention also provides a method of analyzing simultaneously multiple analytes in an unknown fluid and a method of making the apparatus for analysis.

In one aspect, the present technique involves converting the analysis of a large number of analytes to the analysis of a smaller number of chemicals such that the concentration of those smaller number of chemicals can be analyzed using a simple detection method. In an embodiment, certain ions are sensed via a chemistry that changes the pH in a sensor by the ions. In another embodiment, certain chemicals are sensed via a chemistry that changes the concentration of oxygen in the sensor.

Using the technique of the present invention, one can advantageously use a compact detecting instrument to conveniently sense the concentration or presence of a multitude of analytes simultaneously even though the analytes may interfere with one another. Because of the unique feature of using chemical conversion to render the sensing of many analytes into the sensing of a few common chemicals or ions (e.g., oxygen and hydrogen ion), the same chemistry or detection technique can be used to determine the concentration or presence of these few common chemicals and ions. As a result, a smaller number of light source for interrogating the sensors and a smaller number of types of detectors can be used for detection of changes in the sensors. Such factors will result in simpler and more compact apparatuses for analyzing analytes.

The present technique is particularly useful in medicine. An example of fluids that could be analyzed using the devices and methods of this invention is blood. Convenient measurement of blood analytes will greatly enhance the ease and convenience of monitoring the health status of patients. Multiple analytes to be measured in such an exemplary fluid can includes pH, $PO_2$, $PCO_2$, $K^+$, $Na^+$, $Ca^{++}$, $Mg^{++}$, glucose, lactate, creatinine, blood urea nitrogen (BUN), Hct, Hb, bilirubin, therapeutic drugs, drugs of abuse, etc. Although the example described below refers to an aqueous fluid, the invention is also applicable to analyzing other fluids such as gases or other liquids. The invention applies more particularly to a skin-pricking device that is capable of transporting fluid from the skin. Further, the present invention is applicable for analyzing fluids in nonmedical fields, such as environmental samples, samples in manufacturing processes, etc.

DETAILED DESCRIPTION OF THE INVENTION

The present invention involves a technique to more conveniently sense multiple analytes in an unknown fluid sample. The invention is particularly advantageous in that it takes into account the interference of the different analytes on one another in the analysis of the unknown sample.

Figure 1:
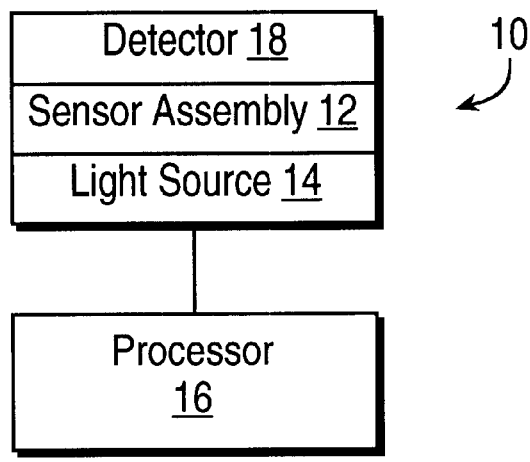
FIG. 1 is an embodiment of a schematic of an apparatus of the present invention.

FIG. 1 shows an embodiment of a device of the present invention for sensing multiple analytes simultaneously. The sensing device 10 includes a sensor assembly 12, which is interrogated by a light source 14 that shines and directs light of suitable wavelength (frequency) profile to the sensor assembly 12. The light source 14 is preferably controlled by a processor 16 to provide light at the desired wavelength and duration to interrogate the sensor assembly 12, causing a light interaction with the sensors in the sensor assembly 12. A light detector 18 detects light resulting from the light interaction at the sensor assembly 12. Signals from the light detector 18 are conveyed to a processor, preferably the same processor 16, for analysis to determine the presence and/or concentration of analytes in the unknown sample.

It is commonly known that some analytes cause absorption of light of certain wavelengths, and some analytes produce changes in fluorescence of a detector molecule. Thus, it is contemplated that both light absorption and fluorescence can be used for sensing the presence and concentration of certain analytes. As used herein, the term "light interaction" refers to light absorption, fluorescence, phosphorescence, luminescence, and the like, as long as a light is irradiated on a sensor in the sensor assembly 12 in the presence of the unknown fluid sample and a detector can be used to detect light changes in the sensor. For illustrative purposes, an example of luminescence will be described in detail. It is to be understood that a person will be able to sense other types of light interaction to determine the presence and concentration of analytes in view of the present disclosure.

In one aspect, the present invention provides a novel technique of measuring one or more analytes in a sample using an assembly of two or more sensors. The sensors themselves may individually respond to more than one analyte. The individual sensors in the sensor assembly can be designed according to this invention in such a way that by using multiple sensors and mathematically processing their output, the concentration of one or more analytes can be precisely determined.

Figure 2:
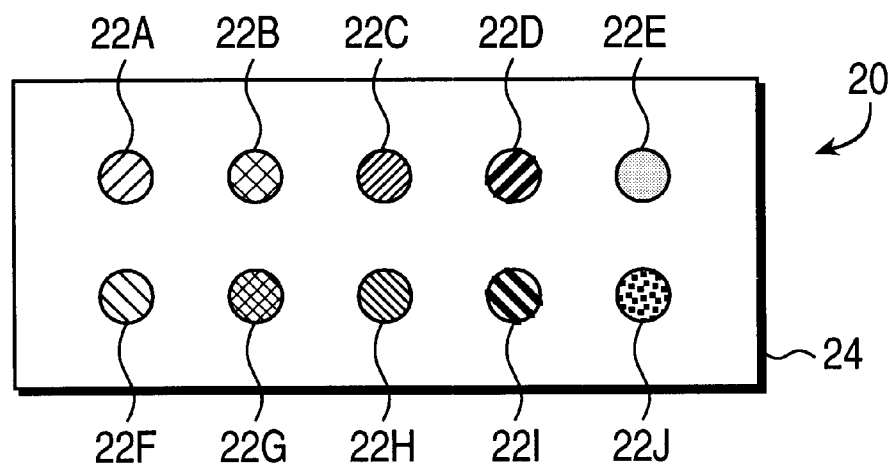
FIG. 2 shows an embodiment of a sensor assembly (e.g., array of sensors) of the present invention.

FIG. 2 illustrates an embodiment of a sensor assembly (e.g., array of sensors) of the present invention. The sensor array 20 includes an array of optical sensors 22 (which include sensors 22A, 22B, 22C, 22D, 22E, 22F, 22G, 22H, 22I, 22J) arranged on a support substrate 24. It is to be understood that it is not necessary to arrange the sensors in a neat rows and columns fashion. Each sensor (22A–22J) includes a sensor matrix confining chemicals that contribute to the light interaction in the presence of a suitable analyte when light from the light source 14 impinges thereon. An adequate number of sensors are included in the sensor assembly (array in FIG. 2) to provide adequate signals on all the analytes of interest.

Because some of the sensors targeting certain analytes may not be entirely independent of the effect of other analytes on the sensors, if desired, there may be more than one sensor targeting a particular analyte. Sensors that target the same analyte may detect the concentration or presence of the analyte by a different mechanism of chemical interaction such that the effect of other analytes will be different on these sensors targeting the same analyte. There is at least one sensor targeting a specific analyte of interest. The sensors that target the same analyte can be considered to be in a group. It is contemplated that in some cases a group that targets a particular analyte includes only one sensor.

Figure 4:
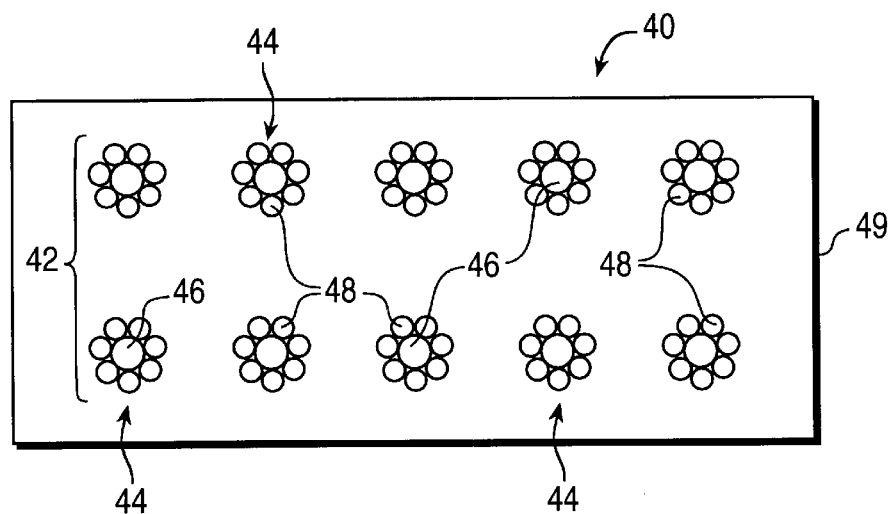
FIG. 4 shows an embodiment of the light source and detector assembly device of this invention.

The invention also teaches a method of designing the individual sensors in such a way that the sensors can be interrogated using a single optical source-detector combination. Thus the invention allows one to measure one or more analytes using two or more sensors that are not entirely specific to the analytes of interest (i.e., not free of interference from other analytes). FIG. 4 shows the preferred embodiment of the light source and detector assembly device ('assembly') of this invention. The assembly 40 includes an array 42 of light source and detector clusters 44, each of which including a light source 46 and detectors 48, situated on a body 49. Preferably, each light source 46 is physically located in such a way that the emerging light from the light source 46 is at least partially delivered to the corresponding optical sensor 22A, etc., in the sensors 22 arrangement. Optical characteristics (wavelength range and intensity) of this light are at least partially matched to overlap the absorption spectrum of fluorescent elements in FIG. 4. The detectors of the clusters are physically arranged in such a way that at least some of the fluorescent radiation emerging from each of the sensors 22A, 22B, etc., in the sensor arrangement 22 impinges on one or more of the detectors 46 of the cluster 44 that corresponds to the specific sensor. Thus, when the assembly 40 is coupled to the sensor array 20, each cluster 44 faces a particular sensor 22A, 22B, etc., in the sensor array 20. It is understood that certain optical elements such as lenses and diffraction gratings may be utilized for efficiency and convenience of directing the radiation to and from the sensor and source-detector elements.

The light sources on the of FIG. 4 may be vertical cavity surface emitting lasers (VCSEL), laser diodes, light emitting diodes, incandescent sources, combination thereof, or any other means of light radiation. The detectors may be solid state diodes, charge couple devices, CMOS detectors, any combination thereof, or similar means of detection. One or more VCSELs and a number of detector diodes may form a cluster dedicated to interrogating a specific sensor. In such a cluster, the VCSELs may be surrounded by a number of detectors. Alternatively, instead of an array of clusters, a single such cluster may be used to interrogate all the sensors using imaging optics, time-multiplexing, physical movement of the cluster to sequentially interrogate the sensors in the sensor array. The sources and detectors of the array may be controlled by an electronic module, which drives the sources and processes the output of the detectors to produce information about the concentration and/or presence of the analytes of interest. If the sensors are made such that the same excitation light can be used for exciting the fluorophore in the sensors, a single light source can be used to generate light and the light can be transmitted to the various sensors, e.g., through a bundle of optical fibers. In this scheme, a single source of light of a particular wavelength can be used to detect the concentrations or the presence of a variety of analytes. In view of the present disclosure, the choice of optical elements (including light sources and detectors) would be obvious to those skilled in the art of optical design.

Figure 5:
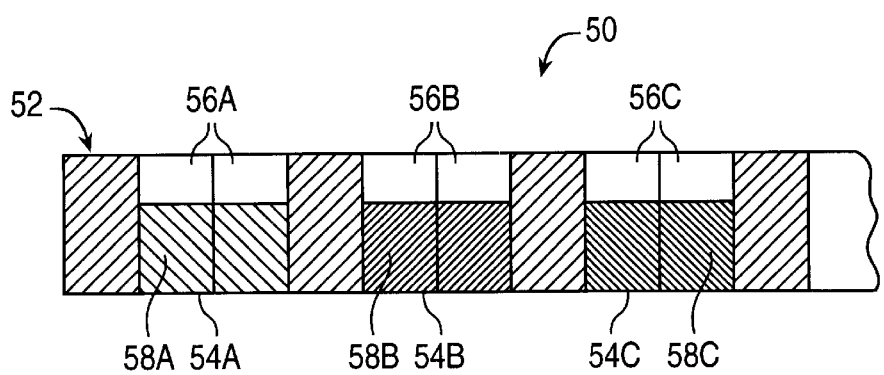
FIG. 5 is an embodiment of an arrangement of sensors according to the present invention.

FIG. 5 is an illustrative example of a sectional view of an embodiment of an arrangement of sensors that can be made for a device similar to that shown in FIG. 1. In FIG. 5, the titer plate 50 includes a support substrate 52 supporting sensors 54A, 54B, 54C, etc., which have membranes 56A, 56B, 56C, etc. respectively. A liquid having analytes of interest can be placed on the titer plate 50 such that the analytes can pass through the membranes 56A, 56B, 56C, etc., and be detected by the appropriate chemistry within the sensors 54A, 54B, 54C, etc., i.e., in the sensor matrices 58A, 58B, 58C, etc. of the sensors. The titer plate 50 can be coupled with a light source/detector assembly 60 similar to assembly 40 such that each light source-detector cluster is coupled to and faces the sensors in the sensor assembly 40. The titer plate 50 can be made such that its size is adequately small such that a drop of a liquid of interest can pass into the sensor matrices of the sensors to be analyzed. The liquid, e.g., blood, can be drawn by capillary action or absorption into the sensor matrices through the respective membranes. For example, if there are N analytes, the concentration and presence of the N analytes can be detected by M sensors $SENSOR_1$, $SENSOR_2$, $SENSOR_3$, $SENSOR_4$ ..., $SENSOR_M$, (where N<=M) each of which has a chemical therein for interacting specifically with a different analyte. As used herein, the terms "chemically interact" and "chemical interaction" when referred to the relationship of an analyte-specific chemical to an analyte to which the chemical is targeted refer to either a chemical reaction such as those through the formation or severance of ionic or covalent bonds, or to the physical changes effecting at the individual molecular level, such as the extent of ionization of a compound or the solubility of a compound. It is to be understood that instead of using optical interrogation involving light sources and detectors, the chemical interaction in the sensors in the presence of a liquid to be analyzed can be detected by electrical means, e.g., using a pH electrode, an oxygen electrode, temperature probe, etc. and the signal of such electrodes can be transmitted by electricity to a processor for record-keeping, display, further data processing, and the like.

Figure 6:
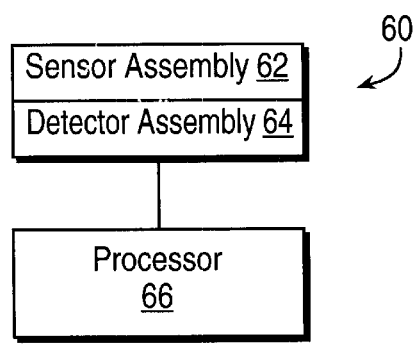
FIG. 6 is a schematic representation of an embodiment of an apparatus for determining the concentration or presence of analytes according to the present invention.

An embodiment of an apparatus for determining the concentration or presence of analytes has a schematic diagram as shown in FIG. 6. The apparatus 60 includes an assembly of sensors 62 that is connected to an assembly of detectors 64. Signals from the assembly of detectors 64 are transmitted to a processor 66 for analysis. The processor 66 can be any computing means known by those skilled in the art, such as electronic computers (e.g., personal computers), microprocessor, minicomputers, mainframe computers, and the like. The processor 66 can also control the irradiation of the sensors by the light source.

The design of each sensor and the number of sensors required in the device are determined by the analytes to be measured, the total number of analytes to be measured, and the number of interfering components. The interfering components are defined as parameters that when changed cause the measurement of an analyte of interest to be affected. The interfering components could be chemical species, pressure, temperature, volume, etc. of the sample. Thus, the number of components interfering could be substantially more than the number of species to be measured (the number of analytes). Although some species of analytes may not interfere with the measurement of any other species, it is possible that one or more species would interfere with the measurement of some other analytes.

In the embodiment of optical interrogation, the design of the sensors is based on the following principles:

(1) Using appropriate chemistry, it is possible to convert changes in an analyte into changes in another species that is easier to sense. Thus, for example, glucose oxidase (an enzyme) changes glucose in the presence of oxygen $O_2$ to form gluconic acid. Formation of gluconic acid changes the pH of the sensing matrix in proportion to the glucose concentration. Moreover, since oxygen is consumed in this reaction, the glucose concentration is also proportional to the change in oxygen concentration in the sensing matrix. Thus both pH and oxygen sensors can be used to make glucose measurements. This would separate the influence of parameters that affect one but not the other of pH and oxygen. Similarly, using an ion selective membrane encapsulating a weak acid, the changes in the ion concentration can be converted to changes in pH of the membrane. Using a series of membranes selective to different ions, such sensors can be designed for different ionic species. Thus, a large number of species can be analyzed using a pH sensor or an oxygen sensor or both. Methods of converting changes in any given analyte into changes in pH or oxygen are well known in chemistry and such changes are taken advantage of in the present invention to use a small number of sensors to sense analytes that might interfere with the sensing of one another. (A brief description of the chemistry of measuring analytes based on oxygen and pH will be provided below). Further, ion selective membranes can be selectively employed by one skilled in the art to confine specific ions of interest.

(2) It is possible that the pH and the oxygen concentrations of the sample itself change. In this case the measured changes will be composite of changes in several analytes. This invention teaches ways of making and choosing multiple pH sensors and multiple oxygen sensors that can be used in an assembly (e.g., array) of sensors. The signals for the individual sensors in the assembly (say, an array) can be processed using computational techniques to determine precisely the concentrations of the analytes in the sample.

(3) pH and oxygen concentrations in different sensors could be different because of their chemical nature or because of buffers used for sensing a particular analyte. Moreover the dynamic range over which these parameters (pH or oxygen) change in the sensor matrices will also be different depending upon the particular sensing chemistry used. In this invention, several different pH and oxygen sensors can be optimized for different dynamic ranges. Thus one can choose a sensor for a given matrix (substance in which the analyte can pass through into the sensor to interact with detecting chemistry) based on the dynamic range over which its pH or oxygen concentration in that matrix will change in response to the analyte of interest. The signals for these sensors have orthogonal components and can be mathematically processed for total analysis.

(4) In this invention, the sensing of analyte can be done in such a way that the pH and oxygen sensors can be interrogated using only one set of optical source(s) and detectors or an array of identical sources and detectors. A preferred embodiment of sensing is based on fluorescence lifetime decay measurements of a ruthenium complex. This fluorophore is attractive because it has long lifetimes that are easier to measure. Moreover, the fluorophore can be interrogated with readily available blue laser diodes and detectors or other solid state devices. This further simplifies the instrumentation. It is understood that there are other fluorophores with similar characteristics and can be adapted for the practice of this invention. Such a modification would be obvious to those familiar with the art of fluorescence sensing.

In implementing the above principles, each of the sensor matrices contains one or more of the following elements: 1) A principal matrix component such as a hydrophilic or hydrophobic polymer with or without one or more modifiers. A modifier may be a plasticizer, a buffering solution, a filler or any such species that improves the functionality of the sensing elements. For example, a plasticizer may be included in a polymer matrix to improve mobility of the analyte or a complex thereof into or within the matrix and a filler may be included to modify the physical property such that the matrix will have the desired physical strength and dimensional stability. Buffers may be added to control the pH. 2) A recognition element that changes its chemical state or conformational state with high specificity in response to the analyte of interest. Such a recognition element may be an analyte-specific chemical that has a more specific chemical recognition interaction with an analyte of interest than with other analytes suspected to be in an unknown sample to be analyzed. The recognition element will be described in more detail later. An example of such an analyte-specific chemical is an ionophore such as valinomycin, to which potassium ion, $K^+$, can bind. 3) A chemical element that changes its chemical state as a function of the number of the recognition events, the changed state itself being an optically absorbing species. An illustrative example of such a chemical element is a dye or chemical indicator such as Bromothymol Blue, which changes color as the pH changes. 4) A chemical element that fluoresces in proportion to the amount of excitation radiation delivered to it, the frequency characteristics of the emitted fluorescent radiation being at least partially matched to the optical absorption characteristics of the changed state of the element in 3).

The matrix described in 1) above, also serves to co-locate the elements in 3) and 4) in a chemical environment that optimizes the interaction between them, thereby maximizing the signal to noise performance of the sensor elements.

In designing a detector for sensing multiple analytes, many sensors have to be implemented in a single detector together. Since the performance of some of the sensors may be affected by more than one parameter, such as pH, oxygen concentration, the concentration of other ions such as potassium, calcium, and the like, a plurality of sensors each being different from other sensors by having a difference in one of the four elements can be used. Table 1 shows examples of typical components of the elements 1 to 4 that can be included in the sensor matrix of the preferred embodiment of this invention. In designing a sensor at least one component from each of the columns has to be selected. These elements can be combined in several ways to make different sensors of the array. Each of the sensors formed this way responds to (i.e., targets) one principal analyte and may have interference from one or more of the other sample parameters. The selection of the elements to be included in a sensor is done such that the sensor based on a given composition has a response that is preferably not proportional to any other sensor's response to a particular change of environmental parameter, e.g., a change in oxygen concentration. In other words, the response of the sensor to a particular environmental change has a component that is preferably orthogonal to the response of other sensors (which have other combinations of the elements in the sensor matrix) to the same environment change. Thus, a sufficiently large number of these combinations can be selected to make an assembly that allows complete and accurate analysis of the desired analytes in the sample. Of course, redundant sensors that respond to an environmental change in a way that is proportional to the response of another sensor can be used. However, the following description pertains using the minimum number of sensors to sense a fix number of relevant parameters.

The number of sensors needed to be present in the detector to detect a desired number of parameters depends, among other factors, on the parameters and the technique for measuring them. If to determine the concentration of an analyte a sensor uses a mechanism that is entirely independent of the influence of other analytes, then only one such sensor will be sufficient to measure the analyte, regardless of how many other sensors are needed to measure the concentration of the other analytes. Assuming such an independent sensor produces a signal S for a concentration, C, of the analyte to which the sensor has specific response, the relationship can be represented mathematically as:

$$S=f(C) \qquad \text{Eq 1.}$$

where f is a function that relates the signal S to the concentration of the analyte.

Before using such a sensor for analyzing a sample, the sensor is calibrated to determine the function f. This is usually done experimentally, whereby a mathematical expression for f is developed by fitting the experimental data of signals S generated by the sensor in response to a series of samples with varying concentrations of the analyte and the corresponding concentrations of analyte. The mathematical expression could be purely empirical or one based on some theoretical analysis of functionality of the sensor behavior. The choice of the specific techniques that might be used for calibrating the sensors is widely known in the literature. If such entirely specific sensors are available for each of the analytes in a sample then the number of sensors required to completely analyze a sample is equal to the number of analytes in the sample. Calibration would be a straight forward task of determining the function f for each of the sensors. In that case, for a sample containing n analytes, one would need n such sensors and the signal from each sensor could be used along with its specific function f, determined by calibration, to infer the concentration of the corresponding analyte. The presence of other analytes would have no effect on the analysis.

However, if the signal $S_i$ of the $i^{th}$ sensor in an array is also a function of the concentration of other (interfering) analytes 1, 2, 3, 4 ... m, where m< or =n (i.e., less than or equal to n), then the equation will be:

$$S_i=F(C_i, C_1, C_2, \ldots C_m) \qquad \text{Eq 2.}$$

where F is the function relating the signal generated by the sensor in response to the concentrations of the analytes of interest and the interfering materials. Eq. 2 represents the most general case where the total number of analytes that contribute to the signal of the sensor is m. The present invention teaches methods of designing sensors such that each sensor in the array is primarily responsive to one analyte and may have relatively small response to a limited number of other analytes called interferents (the interfering analytes). Thus m will be typically a small number <10.

It is to be understood that although $C_i$ is referred to as concentration of the $i^{th}$ analyte, it could be a parameter other than concentration. For example, the temperature variation could contribute to the total signal $S_i$. Effects of other parameters such as pressure, humidity, etc., could also be accounted for similarly. Such a sensor generates the total signal $S_i$, which is a function of the concentrations of several analytes including the interfering analytes and other variables such as temperature. Therefore such a sensor cannot be used by itself to analyze the concentration of one analyte in a sample that has other interfering analytes.

Such an array of sensors with multiple interferences can be used to determine the concentrations of on or more analytes in a sample. To calibrate such an array a number of calibrating solutions have to be used. In the most general case the responses of the sensors are not linear or bilinear and hence one cannot linearize Eq. 2. Methods of neural networks can be used in generating the function in Eq. 2 using the required number of calibrating samples. Such techniques are known in the literature.

The present invention further teaches a method of linearizing the response of the sensors such that Eq. 2 can be simplified. Moreover, this invention also teaches a method of making sensors with only a few interferents so that the mathematical formulations relating the sensor response to the analyte and interferent concentrations are simplified and simple matrix manipulations can be used to generate a model that can be used to determine the analyte concentrations.

As an example, an oxygen sensor based on fluorescence quenching of ruthenium tris diphenyl phenanthroline is generally not affected by the presence of ions and other gases. Thus, only one sensor specifically targeting oxygen concentration need to be present. However, glucose concentration, and concentration of metabolites such as lactate can be measured by sensors that are also affected by oxygen concentration or pH changes. Also, sensors can be made using ionophores, indicator dyes, and fluorophores as described below. Such ion sensors may be affected by pH. Thus, knowing the specific analytes of interest and selecting the corresponding ionophores, indicators, and the fluorophores in a sensor, it is possible to determine what parameters may affect the sensor performance, that is, what analytes may act as interferents. Eq. 2 can then be simplified for the specific well defined samples. An array thus designed can be easily calibrated using the simplified form of Eq. 2 and an appropriate modeling technique such as neural nets. A further simplification of the model is taught later based on the sensor functioning discussed below.

pH Sensors

Optical pH sensors can be based on light absorbance or fluorescence changes of a weakly dissociating dye in response to changes in pH. A weakly dissociating dye HA (in acid form) in solution is in equilibrium with its base form $A^-$ according to the equation $$HA \leftrightarrows A^- + H^+ \qquad \text{Eq. S1.}$$

With brackets indicating the concentration of a substance, let $[A^-]$ be the concentration of $A^-$, $[H^+]$ be the concentration of $H^+$, and $[HA]$ be the concentration of HA, the equilibrium constant Ka for this reaction is $$Ka = [A^-][H^+]/[HA] \qquad \text{Eq. S2.}$$

Since $pH = -\log[H^+]$ and $pKa = -\log Ka$, $$pH = pKa - \log[HA]/[A^-] \qquad \text{Eq. S3.}$$

In a sensor in which a fixed amount of the dye is C, which may be the case if the dye is immobilized in a matrix, in the absence of bleaching and other losses of the dye, C remains constant and $$C = [HA] + [A^-] \qquad \text{Eq. S4.}$$

This leads to the following:

$$pH = pKa + \log\{C/[HA] - 1\} \qquad \text{Eq. S5.}$$

Thus, the pH can be measured by measuring the concentration of either form of the dye, i.e., [HA] or $[A^-]$.

In some pH sensitive dyes, such as phenol red, the acid form and the base form absorb radiation in the different spectral regions. Thus, for phenol red the acid form has an absorption peak at about 430 nm and the base form has an absorption peak at about 550 nm. According to the Beer-Lambert Law:

$$\text{Absorbance } [A^-] = \epsilon L \ [A^-] = \log Io/I \qquad \text{Eq. S6.}$$

where $\epsilon$ is the molar extinction coefficient of $A^-$, L is the length of the path traveled by the light, and Io and I are the intensities of the transmitted light when $A^-$ is absent and present, respectively.

Combining Eq. S5 and Eq. S6, one arrives at:

$$pH = pKa - \log\{C\epsilon L/\log(Io/I) - 1\} \qquad \text{Eq. S7.}$$

Eq. S7 yields an S shaped curve relating pH to the ratio of intensities (Io/I).

In fluorescent dyes such as HPTS (8-hydroxy-1,3,6-pyrenetrisulfonic acid), the energy absorbed by HA and $A^-$ (at wavelengths of about 405 nm and about 470 nm respectively) is emitted as fluorescence at about 520 nm. The relationship between fluorescence intensity, $I_F$, emitted by a sample containing fluorophore concentration C with extinction coefficient $\epsilon$ and fluorescence quantum yield $\Phi$ (the ratio of the number of photons emitted to the number absorbed) is $$I_F = Io\Phi\eta\{1 - \exp(-\epsilon LC)\} \qquad \text{Eq. S8}$$

where $\eta$ is the optical collection efficiency of the instrument. At low absorbance, this equation can be simplified to $$I_F = 2.3 Io\Phi\eta\epsilon LC \qquad \text{Eq. S9.}$$

For a pH sensitive fluorescent dye excited at the absorption peak of the base form the fluorescent intensity, $I_{FA}$ is related to pH by:

$$pH = pKa - \log\{\text{constant}/I_{FA} - 1\} \qquad \text{Eq. S10.}$$

An equation for the acid form of the dye can be derived in a similar way.

$PCO_2$ Sensors

Partial pressure of carbon dioxide, $PCO_2$, is usually measured using the Severinghaus Principle, as shown below. $CO_2$ dissolved in water dissociates to form hydrogen ions ($H^+$) and bicarbonate ions ($HCO_3^-$).

$$CO_2 + H_2O \leftrightarrows H_2CO_3 \leftrightarrows H^+ + HCO_3^- \qquad \text{Eq. S11.}$$

At equilibrium the dissolved concentration of $CO_2$ in an aqueous sample such as blood is proportional to the partial pressure of $CO_2$. The equilibrium constant (dissociation constant) for $CO_2$ in water is $$K_{CO2} = \{[H^+][HCO_3^-]\}/\{[CO_2][H_2O]\} \qquad \text{Eq. S12.}$$

If the medium in which the measurement is made is an aqueous solution of $NaHCO_3$, which dissociates completely into $Na^+$ and $HCO_3^-$ ions, the total concentrations of $HCO_3^-$ and $H_2O$ in the medium remain fairly constant and Eq. S12 can be shown to lead to $$PCO_2 = \text{constant} A\ [H^+] \text{ or } pH = \text{constant} B + \log PCO_2 \qquad \text{Eq. S13.}$$

The above equation indicates that $CO_2$ dissolved in a sample can be measured by measuring the pH of a bicarbonate solution in equilibrium with the sample. To avoid changes in the sample pH from affecting the $CO_2$ measurements, the sensor with the bicarbonate solution and a pH sensitive dye for optical sensing can be encapsulated or separated by a membrane that allows only $CO_2$ to equilibrate with the buffer solution. Such a membrane acts as a barrier to the hydrogen ions in the test sample.

$PO_2$ Sensors

Oxygen is an excellent quencher of fluorescence of many fluorophores. Optical techniques for oxygen sensing can be based on fluorescence quenching of an excited state of a dye (fluorophore) molecule. The excitation of a fluorophore F and its quenching by an oxygen molecule is represented by the following equations:

$$F + h\nu_{ex} \rightarrow F^* \qquad \text{Eq. S14}$$

where h is Planck's constant, $\nu_{ex}$ is the excitation frequency of the radiation and * represent the excited state of a substance.

For radiative decay, $$F^* \rightarrow F + h\nu_{em} \qquad \text{Eq. S15}$$

where $\nu_{em}$ is the frequency of the radiation emitted at the decay of $F^*$.

For nonradiative decay, $$F^* \rightarrow F + \Delta H \qquad \text{Eq. S16}$$

where ΔH is the change in enthalpy. When the fluorescence is quenched by collision with oxygen molecules, we have $$F^* + \tfrac{1}{2} O_2 \rightarrow F + O^* \qquad \text{Eq. S17}$$

and $$O^* \rightarrow \tfrac{1}{2} O_2 + \Delta H \qquad \text{Eq. S18.}$$

Thus, the amount of oxygen present can be determined by measuring the oxygen quenching of an excited form of the fluorophore.

The rate of decay of an excited fluorophore F* after instantaneous excitation is $$d/dt[F^*]_o = -(\gamma + \kappa)[F^*]_o \qquad \text{Eq. S19}$$

where γ and κ are rate constants for radiative and nonradiative decays (i.e., without quencher). Under continuous illumination a constant population of the excited fluorophores, i.e., F*, is established.

In the absence of a quencher (represented by a suffix "o")

$$d/dt[F^*]_o = f(t) - (\gamma + \kappa)[F^*]_o = 0 \qquad \text{Eq. S20}$$

where f(t) is the constant excitation function.
With the presence of a quencher, the equation becomes:

$$d/dt[F^*] = f(t) - \{(\gamma + \kappa) + k_q[Q]\}[F^*] = 0 \qquad \text{Eq. S21}$$

where $k_q$ is the rate constant of the reaction represented by Eq. S17 (rate of quenching) and [Q] is the concentration of the quencher $O_2$. Eliminating f(t) and writing (γ+κ) as $1/\tau_o$, where $\tau_o$ is the lifetime of the fluorophore in the absence of a quencher, the result is:

$$[F^*]_o/[F^*] = 1 + k_q \tau_o [Q] \qquad \text{Eq. S22.}$$

Assuming the rate of nonradiative decay does not change in the presence of quencher and that the intensity of fluorescence is proportional to the number of radiating fluorophores, the equation can be written as:

$$I_{Fo}/I_F = 1 + K_{SV}[Q] \qquad \text{Eq. S23}$$

where $K_{SV}$ equals $k_q \tau_o$ and is known as the Stern-Volmer constant and Eq. S22 and Eq. S23 are variations of the Stern-Volmer equation. Thus, by measuring the intensity of the fluorescence emission by a continuously excited fluorophore the concentration of the quencher such as oxygen can be measured using the Stern-Volmer equation.

For lifetime measurements the fluorophore can be excited by a delta function and the rate of fluorescence decay is observed. According to Eq. S20 the lifetime of the fluoresce decay in the absence of fluorophore is $$\tau_o = 1/(\gamma + \kappa) \qquad \text{Eq. S24.}$$

In the presence of a quencher, the lifetime is $$\tau = 1/(1/\tau_o + k_q[Q]) \qquad \text{Eq. S25}$$

and $$\tau_o/\tau = 1 + K_{SV}[Q] \qquad \text{Eq. S26}$$

which is the lifetime form of the Stern-Volmer Equation and can be used to determine oxygen concentration using lifetime measurements.

Electrolyte Sensors

Cations such as $Na^+$, $K^+$, $Ca^{++}$, and $Mg^{++}$ can be measured optically on very similar principles. Typically one selects an ion selective ionophore. Such ionophores are lipophillic inclusion compounds which typically have a ring-like structure. In such a compound, the ring has several slightly electronegative atoms such as oxygen in it. The size of the ring and the total number of the oxygen atoms determine the relative preference (selectivity) of the ionophore to the cations of various sizes and charged states. Another class of ionophore undergo conformational changes upon selective binding of a cation. Thus a double crown ether based ionophore called BME-44 forms a clam shell like enclosure for an included potassium ion. BME-44 has two crown ethers connected by a 3 carbon chain. When a potassium ion is present, the two crown ethers fold over to form the clam shell. However, the present invention is applicable independent of the scientific theory on ionophores.

These ionophores are lipophillic and are sequestered in a hydrophobic polymer such as polyvinylchloride (PVC) along with a large amount of plasticizer. The ionophores extract the selective ion from the aqueous solution in contact with the polymer surface. Because the ion finds itself in a more favorable energy environment in the ionophore than in the aqueous surrounding, it readily enters the hydrophobic phase of the polymer. However, this causes a charge imbalance in the polymer phase and at the surface of the polymer. The excess charge build-up in the polymer can be used to expel another less favored cation such as $H^+$ from the polymer phase. Alternatively, a charged double layer is formed at the surface of the polymer. The number of cations expelled or the potential gradient at the surface is proportional to the concentration of the cation in the aqueous solution. Similar ionophores are also available for some anions such as chloride ions. Extraction of an anion into the polymer phase will cause another anion to be expelled or a cation such as an hydrogen ion to accompany the anion into the polymer phase.

The potential build up at the surface of the polymer can be measured optically using potential sensitive dyes. The fluorescence of some dyes, such as rhodamine B, is a strong function of the electrical charge in its vicinity. Thus, measurement of the fluorescence changes of a polymer film in which such a dye is immobilized along with an ionophore can be used to measure the concentration of the selective ion in a sample.

As mentioned above, extraction of a positive ion into a hydrophobic polymer by an ionophore can be made to expel another cation such as an hydrogen ion. Thus, if a pH sensitive dye such as HPTS of phenol red or bromothymol blue is located within the polymer, the dye will lose an hydrogen ion when a cation is extracted from the sample by the ionophore. Thus the optical absorption or the fluorescence emission of the dye will change as in the pH sensors described above. Reverse of this effect can be used to determine the concentration of anions.

The folding of BME-44 in the presence of potassium ion can be made to bring a fluorophore such as rhodamine and a quencher such as fluorescein closer together. In this configuration the Foerster energy transfer from the fluorophore to the quencher causes the change in fluorescence in proportion to the number of potassium ions extracted. When an electron donor is placed between a fluorophore and an ionophore (for cations), the ability of the donor to transfer an electron to the excited fluorophore is blocked when a cation is located in the ionophore. Thus when there is no cation in the ionophore, the fluorescence process is nonradiative. When a cation is captured by the ionophore, the electron transfer to the fluorophore is blocked and the fluorescence energy is radiatively emitted.

Metabolite Sensors

Metabolites such as glucose, lactate and creatinine are measured using enzymatic conversion of these species (substrates) into another molecule such as hydrogen peroxide. Alternatively, the enzymatic conversion of the substrates is accompanied by consumption of another species such as oxygen. Thus sensor measuring the concentration of any of these generated or consumed species can be used to determine the concentration of the substrate.

Glucose is converted into hydrogen peroxide while consuming oxygen by glucose oxidase (GOD) according to the following equation:

$$\text{Glucose} + \text{GOD} + O_2 \rightarrow \text{gluconic acid} + H_2O_2 \qquad \text{Eq.S27.}$$

Lactate is converted into pyruvate catalyzed by lactate dehydrogenase and mediated by NAD generating hydrogen ions:

$$\text{Lactate} + \text{NAD} \rightarrow \text{Pyruvate} + \text{NADH} + H^+ \qquad \text{Eq. S28.}$$

Creatinine can be measured using a multienzyme assay involving the following reactions:

$$\text{Creatinine} + H_2O \rightarrow \text{Creatine}$$
(enzyme: Creatinine Amidohydrolase)     Eq. S29

$$\text{Creatine} \rightarrow \text{Sarcosine} + \text{Urea}$$
(enzyme: Creatine Amidinohydrolase)     Eq. S30

$$\text{Sarcosine} + H_2O + O_2 \rightarrow \text{Glycine} + \text{HCHO} + H_2O$$
(enzyme: Sarcosine Oxidase)     Eq.S31.

Equations S27 through S31 indicate that glucose and creatinine can be measured using oxygen sensing methods discussed above. However, the oxygen tension in a sample like blood can vary considerably. It is therefore preferred to make this reaction oxygen independent. In glucose sensing this is achieved by using a mediator such as ferricyanide which replaces oxygen. For measuring lactate, a pH sensor can be used. Here a change in pH of the sample will also affect the measurements of lactate. In these situations it is necessary to measure the $PO_2$ and pH of the sample and correct for the interferences.

Based on the above, sensor matrices can be made using combinations of matrix material, analyte-specific chemicals, indicator dyes, and fluorophores. Table 1 show a list of illustrative examples of these materials that can be selected.

TABLE 1

Examples of composition of typical sensor matrices

| (1) Matrix material Element | (2) Analyte-specific Element | (3) Indicator Element | (4) Fluorophore Element |
|---|---|---|---|
| A Hydrogel such as Poly(acrylamide) or Poly(HEMA), Aerogels, Xerogels, Silica Gels, Ethyl cellulose, PVC, Silicone Rubber and its derivatives, Polyamide and its derivatives, Silica particles, Phase transfer agents, Plasticizers | Bromothymol Blue, Ionophores such as Valinomycin, Monensin, TDMA-Cl | Alizarin or Mordant 11, Alizarin Red S or Mordant Red 3, Bromothymol Blue, Alkali Blue 6B, Arsenazo III, Brilliant Green, Chlorophenol red, Malchite green, Methyl purple, α-Naphtholphthalein, Nitrazine yellow, Resazurin, Tetrabromophenol blue, Thymol blue | Ru(II)-Tris (4,4'-diphenyl-2,2'-bipyridyl) Chloride, Ru (II)tris-4,7-diphenyl-1,10 phenanthroline perchlorate, Ru-tris(diphenyl-dipyridyl) perchlorate, Or any other derivatives of Ruthenium tris or bis compounds with phenanthroline or pyridyl ligands. |

A different matrix material can be selected on the basis of its solubility for the analyte, and the rate of diffusion of the analyte in the matrix. The analyte-specific element can be selected to target the specific analyte of interest, and if desired, in such a way as to minimize the influence of other analytes on the sensor. For example, for sensing pH in the physiological range a pH sensitive dye such as bromothymol blue would be adequate. However, in sensing the change in pH due to glucose oxidation by glucose oxidase in a glucose sensor, a different dye that has a pK which is matched to pK of this oxidation reaction is preferably selected. Moreover, as mentioned earlier, the optical absorption wavelength range of this dye should overlap the fluorescence emission wavelength of the fluorophore of element (4). Such a dye (indicator element) may be selected from those listed in Table 1. Information about the pKs and optical absorption ranges of several pH sensitive indicators is available readily in the literature (e.g. *Sigma-Aldrich Handbook of Stains, Dyes and Indicators* ISBN Number 0-041633-22-5). The description of such dyes and application is herein incorporated by reference. It is also known to those skilled in the art of optical indicators as to how some dyes can be chemically modified to adjust the pK and/or the optical absorption wavelength range. Such modification can be done to meet the requirements of this invention.

The fluorophores can be selected to function in a range of excitation wavelength and fluorescence wavelength of interest. For example, a series of fluorophores listed in the $4^{th}$ column of Table 1 can be excited by a common optical source. Moreover, these fluorophores also have large (0.5–4 milliseconds) fluorescence decay lifetimes, which lie in a short enough range to be measured using only one optoelectronic configuration. Other fluorophores of this type in literature can often be used instead (e.g. Atlas of Fluorescence Spectra and Lifetimes of Dyes attached to Protein, *Analytical Letters*, 18(A4), 393–421 (1985). Moreover, it is obvious to those familiar with the art that other dyes can be modified to adjust the excitation, emission wavelengths and the lifetimes so as to meet the needs of this inventions. It is contemplated that such modified dyes be used in the practice of this invention.

In the fabrication of sensors, as aforementioned, many analytes of interests, such as in a physiological liquid (e.g., blood, saliva, urine, etc.) can be measured via changes in pH and oxygen measurement. Buffering techniques and enzymatic conversion, ionophore and weak acid combinations (for electrolyte measurement) can be used. This affords the efficiency of interrogation of the sensors. Thus, preferably, at least a portion (for example, one third or more, half or more, or all) of the sensors utilizes the measurement of $O_2$ concentration (or presence) or the pH measurement to derive the concentration or presence of the analytes of interest. Table 2 shows an illustrative list of analytes of interest and the changes that can be used for determining the concentration of the analytes.

TABLE 2

Use of pH and $PO_2$ Measurement to Analyze Various Analytes

| Analyte of interest | Changes used to measure the analyte |
|---|---|
| $H^+$ | pH (i.e., $H^+$ concentration) |
| $CO_2$ | pH |
| $Na^+$ | pH |
| $K^+$ | pH |
| $Ca^{++}$ | pH |
| $Cl^-$ | pH |
| BUN | pH |
| Glucose | pH |

TABLE 2-continued

Use of pH and PO$_2$ Measurement to Analyze Various Analytes

| Analyte of interest | Changes used to measure the analyte |
| --- | --- |
| O$_2$ | O$_2$ |
| Glucose | O$_2$ |
| Lactate | O$_2$ |
| Creatinine | O$_2$ |

As an example, in an embodiment of a sensor that senses potassium ions, the matrix with the recognition element, dye and fluorophore can be the potassium sensor membrane described by Wolfbeis et al., "Set of luminescence decay time based chemical sensors for clinical applications," *Sensors and Actuators*, B51 (1998) 17–24. The disclosure on dyes, fluorophores, chemistry of fluorescence/absorbance, and construction of sensors in said Wolfbeis et al. journal article is incorporated by reference herein. Such a matrix includes PVC (poly-vinylchloride) with a plasticizer, ionophore of valinomycin, chemical indicator of bromothymol blue, and fluorophore of ruthenium-tris(dipyridyl) perchlorate, i.e., Ru(didipy).

Figure 3:
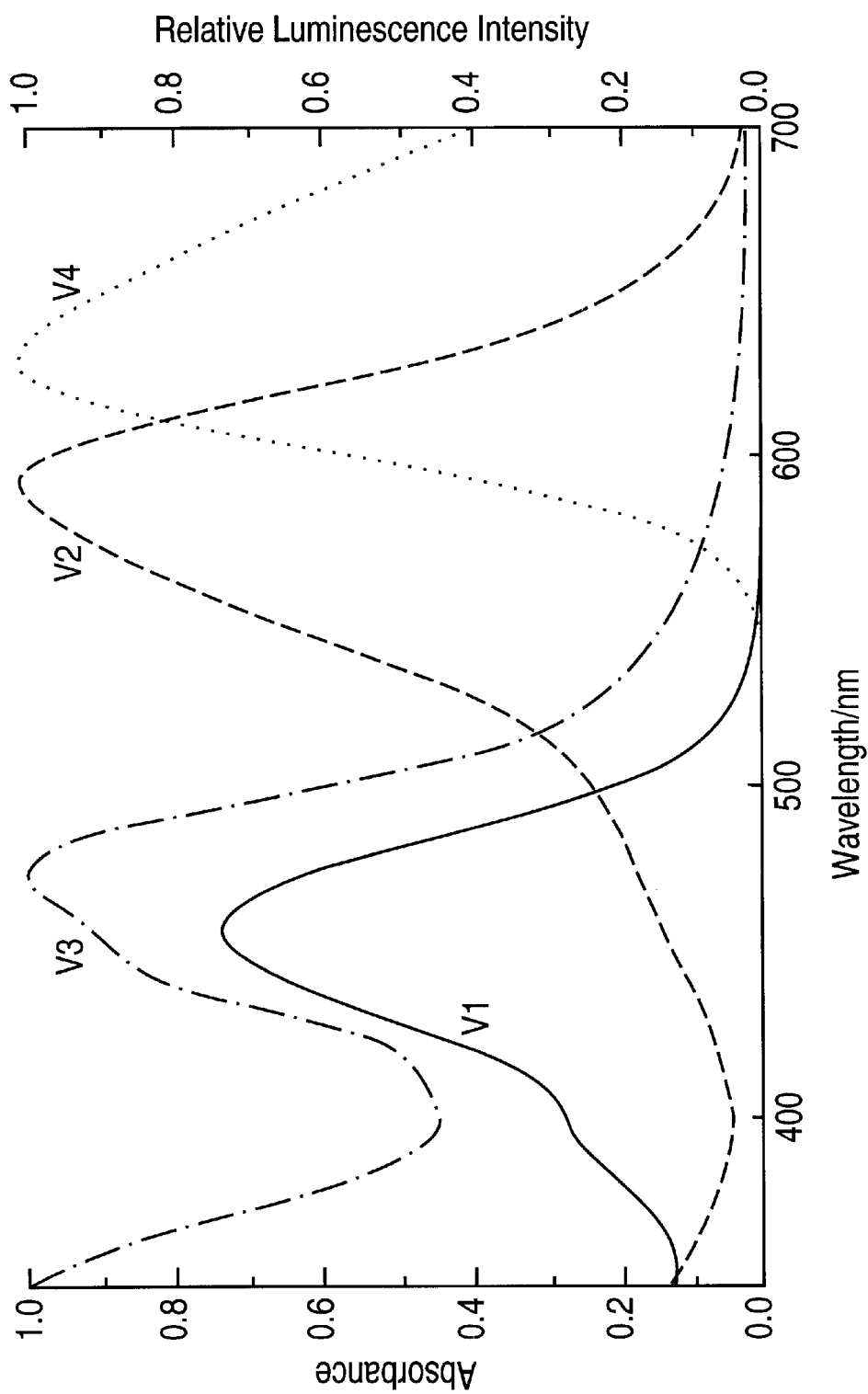
FIG. 3 is a graph showing absorbance and luminescence of a dye under different pH condition.

FIG. 3 is a graph of absorbance and luminescence of the elements in such a system (as disclosed by Wolfbeis et al. supra) showing how it can be used to detect the presence and amount of potassium ions. In FIG. 3, curve V1 is the absorbance of a reactive indicator dye N-9 under alkaline condition about pH 9 (i.e., in alkaline solution). Curve V2 is the absorbance of the dye N-9 under acidic condition about pH 4. These two curves show that as the pH changes, the absorbance peak will move along the frequency (in other words, the wavelength) axis. Curve V3 is the absorbance of the fluorophore Ru complex (i.e., Ru(didipy). Curve V4 is the fluorescence emission of the Ru complex.

According the present invention, taking advantage of the fact that pH changes the absorbance wavelength of the indicator dye, the fluorescence intensity of the fluorophore in a solution can be used to detect the pH change. For example, when the fluorophore is excited by a light of about 470 nm, the fluorophore emits fluorescence at a range peaking at about 630 nm. This fluorescence peak overlaps with the absorbance peak of N-9 at pH 9. Therefore some of the fluorescence light is absorbed by the dye. When K$^+$ is taken up by the ionophore valinomycin, the charge balance requires that the weak acid (valinomycin) expels a H$^+$, thereby leading to a fall in pH. As the pH falls, the absorbance peak of the dye N-9 moves towards shorter wavelengths and therefore absorbs less of the fluorescence of the Ru complex. Furthermore, the N-9 absorbance peak may move close enough to the absorbance peak of the fluorophore Ru-complex to compete with the fluorophore for the excitation light from a light source, further reducing the fluorescence of the Ru complex. Thus the fluorescence emission of the Ru complex can be detected to indicate the change in pH in the solution. Several different indicators can be used in different sensors to sense the same analyte. Obviously, different indicator dyes would have different characteristics of absorbance and different fluorophores would have different excitation and fluorescence characteristics. By the judicious selection of indicator dyes and fluorophores, different sensors can be made to provide different fluorescence emission in the same range or different ranges of pH.

As previously mentioned, an analyte can be analyzed using two or more different chemistry techniques. For example, one glucose sensor can be based on the enzymatic action of glucose oxidase to convert glucose into gluconic acid, which is a weak acid and would lead to a change in pH. Moreover, in the converting glucose to gluconic acid, O$_2$ is consumed and the changes in oxygen content in a sample can be measured to infer the concentration of glucose in the sample. Another example is urea, which can be converted to CO$_2$ and NH$_3$ by the enzymatic action of urease. CO$_2$ dissolves in a bicarbonate solution and changes its pH, which can be measured by a pH sensor. The NH$_3$ formed is consumed by nitrifying bacteria consuming O$_2$. Thus, the urea concentration can be determined by a sensor with nitrifying bacteria and pH sensing capability. For different gases, different matrices (e.g., membranes) can be used to provide different solubility of the gases in the matrices. To sense ions via measuring pH by the technique of using an ionophore specific to the ion of interest and an indicator dye, sensors can be made using several different pH sensitive indicator dyes. These indicator dyes are selected to have different pK's and hence different sensitivity to the pH changes.

Based on Table 1, by selecting ionophores, schemes similar to the sensing of K$^+$ above can be used for sensing other ions. The present invention provides a scheme in which an indicator dye that is sensitive to PO$_2$ can be made to be responsive to pH and vice versa. As previously described, the intensity of fluorescence of certain fluorescence dyes (e.g., Ru(didipy) which fluoresces at a peak at about 620 nm) varies as a function of the quencher (here oxygen) concentration according to the Stern-Volmer equation:

$$FI_o/I_F = 1 + K_{SV}[Q] \qquad \text{Eq. S23}$$

The time constant of a dye such as is also Ru(didipy) is also a function of the quencher concentration:

$$\tau = 1/(1/\tau_o k_q[Q]) \qquad \text{Eq. S25}$$

Several Ruthenium dyes have these characteristics, e.g., Ru(II)-Tris(4,4'-diphenyl-2,2'-bipyridyl)Chloride and Ru(II)tris-4,7-diphenyl-1,10 phenanthroline perchlorate. These Ruthenium complexes and other transition metal complexes are advantageous to use because they have long time constants (e.g., in the order of a few milliseconds) which make them especially attractive for measurement of changes as a result of quenching. The excitation wavelengths of such dyes also render them suitable to be used in conjunction with commercially available laser diode light sources and photodiode detectors.

As shown in FIG. 3, the fluorescence curve of the Ru dye and the absorbance peak of bromothymol blue (BTB) have substantial overlap. Moreover, the absorbance of BTB ($A_{BTB}$) is a function of pH, according to $$pH = pKa - \log\{constant/A_{BTB} - 1\} \qquad \text{Eq. S32}$$

where Ka is the dissociation constant of BTB. BTB has an absorption peak that overlaps with the fluorescence peak of the Ru dyes. The resultant change in fluorescence emission and the accompanying change in fluorescence lifetime will be a function of pH. Equations Eq. S23 and Eq. S32 can be combined and Eq. S25 can be combined with Eq. S32 over the fluorescence-absorbance overlapping region to obtain a relationship of pH to oxygen concentration.

Several pH sensitive dyes have absorbance peak overlap with fluorescence peak of Ruthenium complexes. The following Table 3 is a list of some examples:

TABLE 3

Absorbance of pH sensitive dyes

| Dye | Absorbance, nm region/maximum | pH Ranges |
| --- | --- | --- |
| Alizaria or Mordant red 11 | 500–650/567, 610 | 5.5–6.8, 10.1–12.1 |
| Alizarin Red S, Mordant Red 3 | 490–640/556, 596 | 3.7–5.2 |
| Alkali blue 6B | 500–700/603 | 9.4–14.0 |
| Brilliant Green | 550–700/625 | 0–2.6 |
| Chlorophenol Red | 450–620/572 | 4.8–6.4 |
| Malachite Green | 50–670/614 | 0–2.0, 11.6–14.0 |
| Methyl Purple | 550–67–/620 | 4.8–5.4 |
| α-Naphtholphthalein | 500–72– | 7.3–8.7 |
| Nitrazine Yellow | 450–700/586 | 6–7.2 |
| Resazurin | 500–650/598 | 3.8–6.5 |
| Tetrabromophenol Blue | 500–670/610 | 3.0–4.6 |
| Thymol Blue | 480–670/596 | 1.2–2.8, 8.0–9.2 |
| Thymonaphthelein | 500–689/592 | 8.8–10.5 |
| Bromothymol Blue | 500–700/615 | 6.0–7.6 |

Although not all of the dyes may have high pH sensitivity over the range over which the pH of the sample changes, they may be advantageously used if the matrix in which the dye can act allows little interference from other analytes. For example, a hydrophobic membrane will prevent the passing of ions therethrough. Table 4 shows a table of examples of polymeric substance having various oxygen solubility. By changing the polymer substance one can make sensors with different sensitivities.

TABLE 4

Solubility of Oxygen in Polymers

| Polymer | Solubility of Oxygen, ppm |
| --- | --- |
| Amorphous Polyethylene | 110 |
| Natural Rubber | 160 |
| Polybutadiene | 140 |
| Butyl Rubber | 175 |
| polyvinylacetate | 90 |

EXAMPLE

The following examples illustrate how various elements of Table 1 can be selected to make a sensor array for some of the parameters routinely measured in medical diagnostics.

Examples of Oxygen Sensors

Compositions of the Various Elements of the Oxygen Sensors of This Example

| Sensor Number | Element 1 | Element 2 | Element 3 | Element 4 |
| --- | --- | --- | --- | --- |
| Sensor 1 | PSAR silicone, phenyl triacetoxysilane and L-90 Silica | tris (4,7-diphenyl-1,10 phenanthroline) ruthenium II dichloride | tris (4,7-diphenyl-1,10 phenanthroline) ruthenium II dichloride | tris (4,7-diphenyl-1,10 phenanthroline) ruthenium II dichloride |
| Sensor 2 | General Electric RTV 118 silicone rubber | tris (4,7-diphenyl-1,10 phenanthroline) ruthenium II dichloride | tris (4,7-diphenyl-1,10 phenanthroline) ruthenium II dichloride | tris (4,7-diphenyl-1,10 phenanthroline) ruthenium II dichloride |

Sensor 1: About 0.92 gram of PSAR 148 silicone (obtained form HUELS AMERICA) and 0.13 gram of phenyl triacetoxysilane (HUELS AMERICA) are dissolved in about 4 milliliter of chloroform in a test tube. Next, 0.13 gram of L-90 "Cab-O-Sil" silica from CABOT CORPORATION is added. Then 5.2 milliliter of a solution containing 0.01838 gram tris(4,7-diphenyl-1,10 phenanthroline)ruthenium II dichloride per 100 milliliter chloroform is added. The mixture is homogenized with a BRINKMANN homogenizer. The resultant material can be cast into oxygen sensitive sensor films. This sensor can be illuminated at about 450 nm wavelength and the emitted fluorescence at about 610 nm wavelength or the fluorescence lifetime can be measured. The fluorescence intensity or the lifetime is related to the oxygen concentration as described by the Stern Volmer equation or a suitable modification of the same.

This material composition and other similar compositions for making oxygen sensors are taught in Mauze et al. U.S. Pat. Nos. 5,057,277 and 5,194,391. The synthesis of tris(4,7-diphenyl-1,10 phenanthroline)ruthenium II dichloride is also described in these patents and is incorporated by reference herein.

Sensor 2: About 1.5 grams of commercial silicone rubber (GENERAL ELECTRIC RTV 118) is dissolved in about 4 milliliter of chloroform and about 5 milliliter of a solution containing 0.01838 gram tris(4,7-diphenyl-1,10 phenanthroline) ruthenium II dichloride per 100 milliliter chloroform. The whole mixture is stirred. The solution can be used to cast sensor films as desired. This sensor can be interrogated with an excitation source at about 450 nm wavelength and the emission at about 610 nm wavelength can be measured. Stern Volmer equations or their modifications can be used to represent the relation between the oxygen concentration and the emission intensity or the fluorescence lifetime.

Examples of pH Sensors

Compositions of the Various Elements of the pH Sensors of This Example

| Sensor Number | Element 1 | Element 2 | Element 3 | Element 4 |
| --- | --- | --- | --- | --- |
| Sensor A | Polyurethane hydrogen D4 | Bromothymol blue | Ru (II) Tris (4,4'-diphenyl-2-2'-bipyridyl)-bisbromothymol blue hexahydrate | Ru (II) Tris (4,4'-diphenyl-2-2'-bipyridyl) |
| Sensor B | D4TMI-PEG-jefframine polymer network | [Ru (phen)$_2$ [(phen)-(OH)$_2$]]$^{2+}$ | [Ru (phen)$_2$[(phen)-(OH)$_2$]]$^{2+}$ | [Ru (phen)$_2$[(phen)-(OH)$_2$]]$^{2+}$ |
| Sensor C | D4TMI-PEG-jefframine polymer network | [Ru (ph$_2$phen)$_2$ [(phen)(OH)$_2$]]$^{2+}$ | [Ru(ph$_2$phen)$_2$ [(phen)(OH)$_2$]]$^{2+}$ | [Ru(ph$_2$phen)$_2$ [(phen)(OH)$_2$]]$^{2+}$ |

Sensor A: This sensor is made using an ion pair called Ru (II) Tris(4,4'-diphenyl-2-2'-bipyridyl)bisbromothymol blue hexahydrate, (Ru(dph-bpy)BTB). The preparation of this ion pair and other similar ion pairs that can be used herein to practice this invention is described in "Strategies to Design pH Optrodes with Luminescence Decay Times in the Microsecond Time Regime", Ute Kosch, Ingo Klimant, Tobias Werner, and Otto Wolfbeis, *Analytical*

*Chemistry*, Vol. 70, No 18, Sep. 15, 1998. This article is incorporated by reference herein.

About 4 grams of polyurethane hydrogel D4 (TYNDALL-PLAINS-HUNTER LTD) are dissolved in 72 grams of ethanol and 8 grams of water and stirred for 5 hours. About $2.0 \times 10^{-6}$ M of the ion pair complex, Ru(dph-bpy)BTB is added to this solution and stirred for about 10 minutes. This solution is used to cast pH sensitive films. This sensor can be excited at about 450 nm wavelength and the emission at 610 nm wavelength can be measured. The measured emission intensity or the emission lifetime can be related to the pH by Stern Volmer equation or a modification of the same.

A new class of pH sensors based on [Ru (phen)$_2$[(phen)-(OH)$_2$]]$^{2+}$, (phen complex) or [Ru(ph$_2$phen)$_2$[(phen)(OH)$_2$]]$^{2+}$, (Ph$_2$phen complex), (phen=1,10 phenanthroline, ph$_2$phen=4,7-diphenyl-1,10-phenanthroline, and phen (OH)$_2$=4,7-diphydroxy-1,10-phenanthroline) immobilized in a D4TMI-PEG-jefframine polymer network has been described in "Polymer-Supported pH Sensors Based on Hydrophobically Bound Luminescent Ruthenum (II) Complexes", Jason M. Price, Wenying Xu, J. N. Demas, and B. A. DeGraff, *Analytical Chemistry*, Vol. 70, No. 2, Jan. 15, 1998. The synthesis of D4TMI-PEG-jefframine polymer network is described in Xu, W.; McDonough, R. C. III; Langsdorf, B.; Demas, J. N.; DeGraff, B. A. *Analytical Chemsitry*, 1994, 66, 4133–41. (These articles are incorporated herein by reference.) The resulting sensors can be used in practice of the art covered by this disclosure as described below.

Sensor B: A sensor is prepared by loading D4TMI-PEG-jefframine polymer network, in the form of a film of about 200 micrometers thickness, by soaking the film in a 12 $\mu$M aqueous solution of the phen complex complex for a period of about 24–36 hours. The resultant film can be used as a pH sensor. This film can be excited at 400–500 nm wavelength and the emission can be measured at about 640 nm wavelength. The fluorescence intensity of this film is a function of pH.

Sensor C: A sensor is prepared by loading D4TMI-PEG-jefframine polymer network, in the form of a film of about 200 micrometers thickness, by soaking the film in a 15% aqueous ethanol solution of Ph$_2$phen complex for a period of about 24–36 hours. The resultant film can be used as a pH sensor. This film can also be excited at 400–500 nm wavelength and the excitation can be measured at about 640 nm wavelength. Again, the fluorescence intensity of this film is a function of pH.

Example of Potassium Ion Sensor

Compositions of the Various Elements of the Potassium Ion Sensor of This Example

| Element 1 | Element 2 | Element 3 | Element 4 |
|---|---|---|---|
| PVC,2-cyanophenyldodecyl ether (plasticizer) | Valinomycin | Bromothymol blue | Ru(dph-bpy) |

About 120 mg of polyvinylchloride (PVC), 240 mg of 2-cyanophenyldodecyl ether (plasticizer), 2 mg of valinomycin and 1 mg of Ru(dph-bpy)BTB (described under pH sensor above) are dissolved in 1.5 mL of tetrahydroxyfuran (THF). The sensor is prepared by spreading this solution and casting films. The sensor can be excited at about 470 nm wavelength and the emission can be measured at about 610 nm wavelength.

To measure a plurality of analytes simultaneously, the present invention takes advantage of the fact that the extent of interference is different for different sensors, depending on the chemistry selected for the sensor. Each of the sensors has varying amounts of interference from the species of analytes in the sample. Thus, using a large number of sensors and using correlation techniques the composition of the sample regarding the species of analytes can be determined. Such correlation techniques have been used in other fields of study and we have discovered that they can be adopted for analyte analysis in the present invention.

The above description has shown that the analytes of interest can all be measured using either a pH sensor or an oxygen sensor or both. The Stern-Volmer equations (S23 and S26) show that the sensor signal $\tau$ or $I_F$ is a linear function of the concentration of the quencher [Q]. In the case of the oxygen sensor the quencher is the analyte. In case of the pH sensors and other sensors that measure an analyte concentration based on titration of a pH sensitive indicator (the second element), the sensor signal is a characteristic sigmoidal titration curve (see FIG. 8, Wolfbeis et al., supra). The sensitivity of these sensors is greatest when the measured sensor signal ($\tau$ or $I_F$) lies on the quasi-linear central section of the indicator titration curve. One method of achieving this is by incorporating a weak acid or base (an example is sodium bicarbonate) into the sensor membrane (element (1)), so as to adjust the pH of the sensor in the linear range. Such a component of element (1) effectively shifts the titration curve to enable the sensor to operate in the linear range for the chosen indicator. In the sensor arrays of this invention, a number of sensors differing only in the pK of the indicator or (inclusively) the type and concentration of the acid/base component shifting the titration curve can be used. This ensures that for a given dynamic range of the analyte concentrations, a number of sensors operate in the linear response range. Therefore, from an array one can choose only the linear sensors to perform the mathematical operations for calibration and detection.

Another method well known in the art of analysis is known as "method of standard additions." In this method one adds a sufficient amount of the analytes of interest to shift the concentrations of the analytes in the linear range. Thus, in the sensor arrays of this invention, one could incorporate varying amounts of the analytes in element (1) so that the range over which the analyte concentration lies when a sample is added is linear.

Thus, the methods of this invention can be used to linearize the sensor responses. Hence, calibration and modeling of the sensor arrays can be represented by a linear matrix equation:

$$S = MC \qquad \text{Eq. 3}$$

where S is a column vector representing the signals obtained from n sensors in the array. M is a n×m matrix representing the parameters correlating the sensor signals to the concentrations of the analytes (including interferents). C is then a m×1 matrix containing the concentrations of the analytes in the sample.

In matrix M, only the columns corresponding to the interfering analytes will have non zero values. Thus, when only the pH and oxygen concentrations generate responses from the sensors, only two columns of the matrix M will have non zero-values. When a large number of analytes cause interference in a large number of sensors, the matrix will be more complex.

In any case, such an equation can be solved by chemometric techniques such as PLS. In PLS, the unknown concentration, $C_{un}$, of an analyte can be determined from the signal, $S_{un}$, obtained from the sample by using the following equation:

$$C_{un} = G S_{un} \quad \text{Eq. 4}$$

where G is estimated from the columns of a matrix R of sensor signals in response to a series of calibration samples of concentrations C. The matrix G is then estimated by:

$$G = C R^{+} \quad \text{Eq. 5}$$

where $R^{+}$ is the pseudoinverse of R. As mentioned earlier, the number of analytes to be analyzed may be less than the number of analytes (including interferents) that contribute to the sensor signals. In such cases, it may not be necessary to know the concentrations of the interferents in the calibration samples to generate G. When all the concentrations in C are known, multicomponent analysis may be used to determine the calibration. When only the values of some of the rows of C are known, PLS can be used for calibration.

Mathematically, several methods of finding the pseudoinverse of R can be used by one skilled in the art. The most reliable and comprehensive method is based on singular value decomposition (SVD). The application of this technique to determine $R^{+}$, and hence G is well known in the literature (e.g., *Linear Algebra and its Applications,* Gilbert Strang, Chapter 9, Academic Press, NY).

Once G is determined for a comprehensive set of calibration samples represented by C, Eq. 4 can be used to determine the unknown concentration of any analyte in the sample so long as all the analytes generating the signal from this sample were also present in the calibration set. A processor can be programmed to calculate according to an algorithm implementing the above mathematics. The program can be stored in a medium such as a hard disk, floppy disk, CD-ROM, tape, Zip disk, and the like, or in the processor itself.

Although the above-described embodiments of the present invention have been described in detail, various modifications to the present invention will become apparent to those skilled in the art from the foregoing description and accompanying drawings and will be within the scope of the invention.

What is claimed is:

1. A device for analyzing multiple analytes simultaneously in a fluid, comprising:
   (a) a plurality of sensors each for exposing to a sample of the fluid, the plurality of sensors comprising:
      groups of sensors, each group targeting a specific analyte, each group including one or more sensors including an analyte-specific chemical that interacts more specifically with one analyte than with some other analytes to be analyzed;
   (b) light source for providing light to shine on the sensors of said plurality of sensors to cause light interaction with said sensors, wherein the differences in the sensors lead to differences in said light interaction;
   (c) detectors for determining the light interaction by the sensors; and
   (d) processor for analyzing the light interaction by the sensors to take into account interference in light interaction among the analytes, thereby determining the concentration of each of the analytes in the fluid.

2. A device according to claim 1 wherein at least some of the sensors each comprise a matrix in which the analyte of interest can penetrate, the analyte-specific chemical that chemically interacts specifically with the analyte, a fluorophore that fluoresces at a characteristic frequency, the fluorescence of said fluorophore being affected by the amount of analyte chemically interacting with the analyte-specific chemical.

3. A device according to claim 2 comprising a chemical indicator, wherein the chemical interaction of the analyte with the analyte-specific chemical can change absorption of the chemical indicator at the fluorescence frequency of the fluorophore.

4. A device according to claim 3 wherein in for at least some of the sensors the analyte-specific chemical is not the same as the chemical indicator and the amount of chemical interaction of the analyte-specific chemical with the analyte changes the chemical state of the chemical indicator to affect the absorption thereby at the fluorescence frequency of the fluorophore.

5. A device according to claim 2 wherein more than half of sensors in the plurality of sensors comprise one of a pH sensor and an oxygen sensor and wherein at least one of the groups include sensors having different chemicals interacting specifically with an analyte.

6. A device according to claim 5 comprising sensors that use a pH sensor or an oxygen sensor to determine the concentration of an analyte other than that of hydrogen ion or oxygen.

7. A device according to claim 2 comprising at least some sensors that can detect the concentration of at least five of the following: hydrogen ion, carbon dioxide, oxygen, potassium ion, sodium ion, calcium ion, chloride ion, blood urea nitrogen (BUN), glucose, lactate, and creatinine.

8. A device according to claim 2 wherein the same light source is used to provide light to shine on the plurality of sensors.

9. A device according to claim 2 comprising light outlets each for directing light at a sensor and said outlet is surrounded by detectors.

10. A device according to claim 2 wherein the light interaction includes luminescence decay of fluorescence.

11. A device according to claim 2 wherein the light source includes one of light emitting diode, vertical cavity surface emitting laser, and laser diodes.

12. A device according to claim 2 wherein the processor analyzes the light interaction of the sensors using a matrix algorithm.

13. A device for analyzing simultaneously multiple analytes in a fluid, comprising:
   (a) a plurality of sensors each for exposing to a sample of the fluid, the plurality of sensors comprising:
      groups of sensors, each group having one or more sensors each having an analyte-specific chemical that interacts more specifically with one analyte than with some other analytes to be analyzed, wherein at least half of the sensors for sensing analytes other than hydrogen ions or oxygen include a pH sensor or an oxygen sensor;
   (b) light source for providing light to shine on the sensors of said plurality of sensors to cause light interaction with said sensors, wherein the differences in the sensors lead to differences in said light interaction, wherein at least some of the sensors specific for different analytes receive light of the same frequency profile;
   (c) detectors for determining the light interaction by the sensors; and
   (d) processor for analyzing the light interaction by the sensors to take into account interference in light interaction among the analytes using a matrix algorithm, thereby determining the concentration of each of the analytes in the fluid.

14. A method for analyzing simultaneously multiple analytes in a fluid, comprising:
    (a) exposing a plurality of sensors each to a sample of the fluid, the plurality of sensors having groups of sensors, each group having one or more sensors each including an analyte-specific chemical that interacts more specifically with one analyte than with some other analytes to be analyzed; and
    (b) shining light on the sensors of said plurality of sensors to cause light interaction with said sensors, wherein the differences in the sensors lead to differences in said light interaction;
    (c) detecting the light interaction by the sensors;
    (d) mathematically analyzing the light interaction by the sensors to take into account interference in light interaction among the analytes, thereby determining the concentration of each of the analytes in the fluid.

15. A method according to claim 14 comprising allowing an analyte of interest in the fluid to pass through a matrix in a sensor to chemically interact with the analyte-specific chemical, thereby affecting the fluorescence of a fluorophore in the sensor to indicate the concentration of the analyte in the fluid.

16. A method according to claim 15 comprising using a pH sensor or an oxygen sensor to determine the concentration of an analyte other than that of hydrogen ion or oxygen, and wherein a group has sensors with different chemicals interacting specifically with an analyte.

17. A method according to claim 15 comprising determining the concentration of at least the following: hydrogen ion, carbon dioxide, oxygen, potassium.

18. A method according to claim 15 comprising detecting the concentration of at least five of the following: hydrogen ion, carbon dioxide, oxygen, potassium ion, sodium ion, calcium ion, chloride ion, blood urea nitrogen (BUN), glucose, lactate, and creatinine.

19. A method according to claim 14 wherein the chemical interaction of the analyte with the analyte-specific chemical affects absorption of a chemical indicator at the fluorescence frequency of the fluorophore.

20. A method according to claim 14 comprising using the same light source is used to provide light to shine on the plurality of sensors.

21. A method according to claim 14 comprising directing light from a light outlet at a sensor and detecting fluorescence from the sensor by detectors surrounding said light outlet.

22. A method according to claim 14 wherein the light interaction includes luminescence decay of fluorescence.

23. A method according to claim 14 comprising analyzing the light interaction of the sensors using a matrix algorithm to take into account the interference of light interaction among the sensors.

24. An method of making a device for analyzing simultaneously multiple analytes in a fluid, comprising:
    (a) making a plurality of sensors each for exposing to a sample of the fluid, the step of making the plurality of sensors comprising making groups of sensors wherein each group having one or more sensors including an analyte-specific chemical that interacts more specifically with one analyte than with some other analytes to be analyzed;
    (b) positioning a light source for providing light to shine on the sensors of said plurality of sensors to cause light interaction with said sensors, wherein the differences in the sensors lead to differences in said light interaction;
    (c) positioning detectors for determining the light interaction by the sensors; and
    (d) electrically connecting the detectors to a processor for analyzing the light interaction by the sensors to take into account interference in light interaction among the analytes, thereby determining the concentration of each of the analytes in the fluid.

* * * * *